United States Patent
Kauffman et al.

(10) Patent No.: US 9,415,378 B2
(45) Date of Patent: Aug. 16, 2016

(54) DEHYDROGENATION CATALYST, ITS USE AND METHOD OF PREPARATION

(71) Applicant: Saudi Basic Industries Corporation, Riyadh (SA)

(72) Inventors: James W. Kauffman, Katy, TX (US); Patricia A. Hooks, Houston, TX (US); Balamurali Krishna R. Nair, Sugar Land, TX (US); Xiankuan Zhang, Houston, TX (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 227 days.

(21) Appl. No.: 14/093,630

(22) Filed: Dec. 2, 2013

(65) Prior Publication Data

US 2015/0151283 A1    Jun. 4, 2015

(51) Int. Cl.
*B01J 23/58* (2006.01)
*B01J 37/00* (2006.01)
(Continued)

(52) U.S. Cl.
CPC ............ *B01J 27/1856* (2013.01); *B01J 21/04* (2013.01); *B01J 23/002* (2013.01); *B01J 23/02* (2013.01); *B01J 23/10* (2013.01); *B01J 23/14* (2013.01); *B01J 23/42* (2013.01); *B01J 23/755* (2013.01); *B01J 32/00* (2013.01); *B01J 37/04* (2013.01); *C07C 5/3337* (2013.01); *C07C 2521/04* (2013.01); *C07C 2523/02* (2013.01); *C07C 2523/10* (2013.01); *C07C 2523/14* (2013.01);
(Continued)

(58) Field of Classification Search
CPC .......... B01J 21/04; B01J 21/066; B01J 23/58; B01J 23/626; B01J 23/892; B01J 37/00; B01J 37/0201; B01J 37/08

USPC .................. 502/303, 304, 334, 335, 352, 355
See application file for complete search history.

(56) References Cited

U.S. PATENT DOCUMENTS 2,796,326 A * 6/1957 Gladrow .................. B01J 21/04
                                                    208/138
3,761,531 A    9/1973 Bloch
(Continued)

FOREIGN PATENT DOCUMENTS

| EP | 1952876 A1 | 8/2008 |
| JP | 03260411 B2 | 2/2002 |
| JP | 2011207697 A | 10/2011 |

OTHER PUBLICATIONS

International Search Report for PCT/US2014/068005 (KS20062PCT) mailed Feb. 15, 2015, 5 pages.
(Continued)

Primary Examiner — Patricia L Hailey
(74) Attorney, Agent, or Firm — Cantor Colburn LLP

(57) ABSTRACT

A dehydrogenation catalyst is formed by forming a mixture comprising a bayerite aluminum hydroxide ($Al(OH)_3$), a lanthanum (La) source, a cerium (Ce) source, a barium (Ba) source, a zirconium (Zr) source, and water into a shaped body. The shaped body is calcined at a temperature of at least 750° C. to form a catalyst support. The catalyst support is treated with a dehydrogenation catalyst component to form a treated catalyst support containing the dehydrogenation catalyst component. The treated catalyst support is then calcined. The resulting catalyst composition may be used by contacting a paraffin hydrocarbon feed with a catalyst within a reactor in the presence of steam under dehydrogenation reaction conditions suitable to form dehydrogenated hydrocarbon products.

17 Claims, 1 Drawing Sheet

(51) Int. Cl.
*B01J 37/08* (2006.01)
*B01J 27/185* (2006.01)
*C07C 5/333* (2006.01)
*B01J 37/04* (2006.01)
*B01J 21/04* (2006.01)
*B01J 23/00* (2006.01)
*B01J 23/02* (2006.01)
*B01J 23/10* (2006.01)
*B01J 23/14* (2006.01)
*B01J 23/42* (2006.01)
*B01J 23/755* (2006.01)
*B01J 32/00* (2006.01)

(52) U.S. Cl.
CPC ....... *C07C 2523/42* (2013.01); *C07C 2523/755* (2013.01); *C07C 2523/89* (2013.01); *C07C 2527/185* (2013.01); *Y02P 20/52* (2015.11)

(56) References Cited

U.S. PATENT DOCUMENTS

| | | | |
|---|---|---|---|
| 4,547,618 A | 10/1985 | Forbus | |
| 5,378,350 A | 1/1995 | Zimmermann et al. | |
| 5,413,984 A * | 5/1995 | Marecot | B01J 23/38 423/213.5 |
| 5,922,639 A * | 7/1999 | Alario | B01J 23/56 502/224 |
| 6,007,700 A * | 12/1999 | Alario | B01J 21/04 208/134 |
| 6,414,209 B1 | 7/2002 | Herskowitz et al. | |
| 6,808,652 B2 | 10/2004 | Park et al. | |
| 7,375,049 B2 | 5/2008 | Hayes et al. | |
| 7,482,500 B2 | 1/2009 | Johann et al. | |
| 7,488,858 B2 | 2/2009 | Johann et al. | |
| 2002/0016258 A1 | 2/2002 | Wu et al. | |
| 2003/0191020 A1 | 10/2003 | Bharadwaj et al. | |
| 2010/0312035 A1* | 12/2010 | Ruettinger | B01J 23/002 585/852 |
| 2013/0072739 A1 | 3/2013 | Ruettinger et al. | |
| 2013/0189173 A1 | 7/2013 | Hilgendorff et al. | |
| 2014/0200384 A1 | 7/2014 | Kauffman et al. | |
| 2014/0357471 A1* | 12/2014 | Lacombe | C04B 35/111 502/8 |

OTHER PUBLICATIONS

Written Opinion of the International Searching Authority for PCT/US2014/068005 (KS20062PCT) mailed Feb. 15, 2015, 6 pages.

* cited by examiner

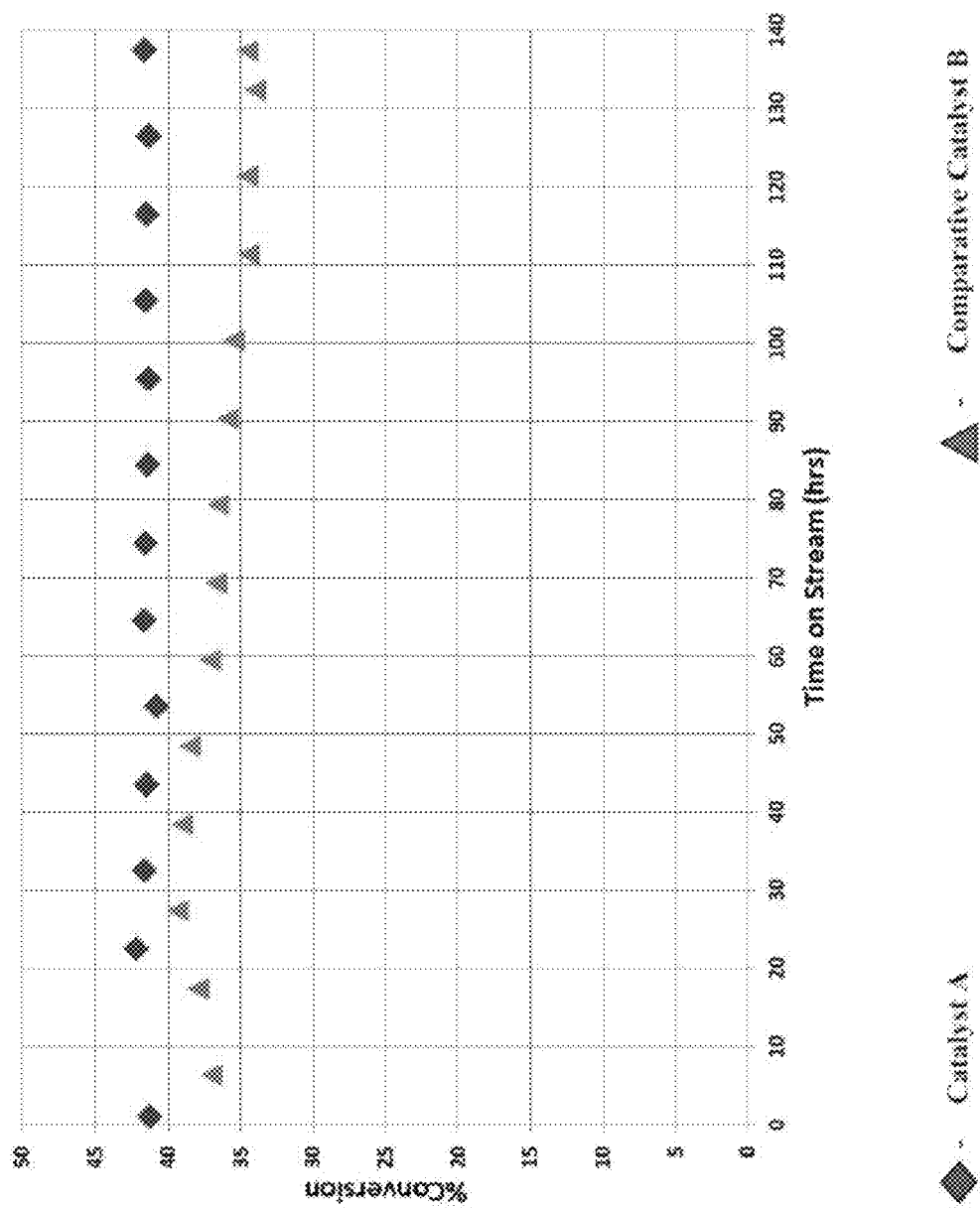

DEHYDROGENATION CATALYST, ITS USE AND METHOD OF PREPARATION

FIELD OF THE INVENTION

The present invention relates to catalysts, their preparation and use, and particularly to those catalysts useful in the conversion of hydrocarbons by dehydrogenation.

BACKGROUND

Dehydrogenation reactions are endothermic reactions and require the input of heat to carry out the reaction. At higher temperatures higher conversion can be achieved. Thus, higher temperatures are often desirable. At higher temperatures, however, coking of the catalyst increases. In the dehydrogenation of hydrocarbons, such as the dehydrogenation of propane to propylene, platinum is generally used for the active catalyst component for steam-based dehydrogenation reactions. In such reactions, the primary cause of catalyst deactivation is due to the buildup of coke on the catalyst and catalyst support surface. The buildup of coke results in thermal decomposition of the alkane/alkene and eventually inhibits the dehydrogenation reaction at the platinum surface. Catalysts that have accumulated too much coke may become unusable or must undergo a regeneration process to bring back the dehydrogenation activity. By providing a low coking dehydrogenation catalyst, higher temperatures may be used that result in higher conversions or that may allow the catalysts to be used for longer periods at lower temperatures, and thus extend the time between regenerations when used. The present invention is therefore directed to providing a low-coking dehydrogenation catalyst that provides these benefits.

SUMMARY

A method of forming a dehydrogenation catalyst is achieved by forming a mixture comprising a bayerite aluminum hydroxide ($Al(OH)_3$), a lanthanum (La) source, a cerium (Ce) source, a barium (Ba) source, a zirconium (Zr) source, and water into a shaped body. The shaped body is calcined at a temperature of at least 750° C. to form a catalyst support. The catalyst support is treated with a dehydrogenation catalyst component to form a treated catalyst support containing the dehydrogenation catalyst component. The treated catalyst support is then calcined.

In certain embodiments, the dehydrogenation catalyst component may be at least one of platinum (Pt), tin (Sn), nickel (Ni), phosphorus (P), and calcium (Ca).

In certain embodiments, the catalyst support may contain various metal oxides. The catalyst support may contain lanthanum oxide in an amount of from 1% to 8% by weight of the catalyst support provided by the lanthanum source of the mixture. The catalyst support may contain cerium oxide in an amount of from 1% to 8% by weight of the catalyst support provided by the cerium source of the mixture. The catalyst support may contain barium oxide in an amount of from 0.5% to 10% by weight of the catalyst support provided by the barium source of the mixture. The catalyst support may contain zirconium oxide in an amount of from 5% to 20% by weight of the catalyst support provided by the zirconium source of the mixture.

In a particular embodiment, the catalyst support contains lanthanum oxide in an amount of from 1% to 8% by weight of the catalyst support provided by the lanthanum source of the mixture, cerium oxide in an amount of from 1% to 8% by weight of the catalyst support provided by the cerium source of the mixture, barium oxide in an amount of from 0.5% to 10% by weight of the catalyst support provided by the barium source of the mixture, and zirconium oxide in an amount of from 5% to 20% by weight of the catalyst support provided by the zirconium source of the mixture.

The catalyst support may be in a substantially eta alumina phase.

In another aspect of the invention, a method of dehydrogenating paraffin hydrocarbons is achieved by contacting a paraffin hydrocarbon feed with a catalyst within a reactor in the presence of steam under dehydrogenation reaction conditions suitable to form dehydrogenated hydrocarbon products. The catalyst support is made by forming a mixture comprising a bayerite aluminum hydroxide ($Al(OH)_3$), a lanthanum (La) source, a cerium (Ce) source, a barium (Ba) source, a zirconium (Zr) source, and water into a shaped body. The shaped body is calcined at a temperature of at least 750° C. to form a catalyst support. The catalyst support is treated with a dehydrogenation catalyst component to form a treated catalyst support containing the dehydrogenation catalyst component. The treated catalyst support is then calcined.

In certain embodiments, the dehydrogenation catalyst component may be at least one of platinum (Pt), tin (Sn), nickel (Ni), phosphorus (P), and calcium (Ca).

In certain embodiments, the catalyst support may contain various metal oxides. The catalyst support may contain lanthanum oxide in an amount of from 1% to 8% by weight of the catalyst support provided by the lanthanum source of the mixture. The catalyst support may contain cerium oxide in an amount of from 1% to 8% by weight of the catalyst support provided by the cerium source of the mixture. The catalyst support may contain barium oxide in an amount of from 0.5% to 10% by weight of the catalyst support provided by the barium source of the mixture. The catalyst support may contain zirconium oxide in an amount of from 5% to 20% by weight of the catalyst support provided by the zirconium source of the mixture.

In a particular embodiment, the catalyst support contains lanthanum oxide in an amount of from 1% to 8% by weight of the catalyst support provided by the lanthanum source of the mixture, cerium oxide in an amount of from 1% to 8% by weight of the catalyst support provided by the cerium source of the mixture, barium oxide in an amount of from 0.5% to 10% by weight of the catalyst support provided by the barium source of the mixture, and zirconium oxide in an amount of from 5% to 20% by weight of the catalyst support provided by the zirconium source of the mixture.

The catalyst support may be in a substantially eta alumina phase. In still another aspect of the invention, a dehydrogenation catalyst composition useful for the dehydrogenation of hydrocarbons comprises a catalyst support of bayerite aluminum hydroxide ($Al(OH)_3$) having a substantially eta alumina phase and containing lanthanum (La), cerium (Ce), barium (Ba), and zirconium (Zr) synthesized within the crystal structure of the catalyst support.

BRIEF DESCRIPTION OF THE DRAWINGS

For a more complete understanding of the present invention, and the advantages thereof, reference is now made to the following descriptions taken in conjunction with the accompanying figures, in which:

FIG. 1 is a plot of the conversion over time for Catalyst A, which has a catalyst support prepared in accordance with an embodiment of the invention, and Comparative Catalyst B when each is a used in the dehydrogenation of propane to form propylene under identical conditions.

DETAILED DESCRIPTION

A useful catalyst composition for the dehydrogenation of hydrocarbon compounds is provided by forming a catalyst composition that utilizes a catalyst support that incorporates certain promoters or materials. The catalyst composition results in better stability and lower coking when the catalyst is used in dehydrogenation reactions. By providing a lower coking catalyst, the dehydrogenation reaction can be carried out at higher temperatures and for longer periods before requiring catalyst regenerations.

Typically, catalyst supports for propane dehydrogenation are inorganic oxides, and in most cases, the substrate is an alumina ($Al_2O_3$) substrate that is a crystalline alumina material, such as eta ($\eta$) alumina, theta ($\theta$) alumina, and gamma ($\gamma$) alumina crystalline materials.

In the present invention, the inorganic oxide forming the support is formed from a bayerite aluminum hydroxide (Al(OH)$_3$) support precursor that results in a support where the primary component of the support is in an eta ($\eta$) alumina phase. In industrial practice, surface area values of alumina materials above 120 m$^2$/g constituting eta ($\eta$) alumina phase and those under 120 m$^2$/g constitute a theta ($\theta$) alumina phase.

The promoters or additional materials are incorporated into the support as an additive used during the formation and synthesis of the support prior to shaping and calcining the catalyst support. This is to be contrasted to the subsequent treatment of a shaped and/or calcined catalyst support with the same promoters or materials. The metal oxide promoters are incorporated throughout the aluminum oxide matrix becoming an integral part of the bulk crystalline phase. Modification of the aluminum oxide crystalline phase both in the bulk structure and at the surface of the crystallites gives the support its unique properties. Whereas in conventional catalyst supports wherein the previously formed support material is subsequently treated by impregnation of the promoter metal oxides results in the promoters laying on top of the alumina surface but not within the alumina oxide crystalline structure.

Specifically, in the present invention, the promoter materials incorporated into the support include lanthanum (La), cerium (Ce), barium (Ba), and zirconium (Zr) and result in the formation of their respective oxides, e.g., $La_2O_3$, $CeO_2$, BaO, $ZrO_2$, in the final catalyst support.

With respect to the lanthanum promoter, the lanthanum of the catalyst support is provided from a lanthanum source. The lanthanum source may be lanthanum oxides, nitrates, carbonates, halogens, organic acids, and other lanthanum salts, which may be in their hydrated or non-hydrated form. A specific example of a suitable lanthanum source is La(NO$_3$)$_3$.6H$_2$O. The lanthanum source used in the synthesis or formation of the catalyst support may provide the final catalyst support with a lanthanum oxide content in an amount of from 1% to 8% by weight of the catalyst support, more particularly from 1% to 4% by weight of the catalyst support, and still more particularly from 1.4% to 2.0% by weight of the catalyst support.

It should be understood that with respect to any concentration or amount range listed or described herein as being useful, suitable, or the like, it is intended to include every concentration or amount within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

With respect to the cerium promoter, the cerium of the catalyst support is provided from a cerium source. The cerium source may be cerium oxides, nitrates, carbonates, halogens, organic acids, and other cerium salts, which may be in their hydrated or non-hydrated forms. A specific example of a suitable cerium source is Ce(NO$_3$)$_3$.6H$_2$O. The cerium source used in the synthesis or formation of the catalyst support may provide the final catalyst support with a cerium oxide content in an amount of from 1% to 8% by weight of the catalyst support, more particularly from 2% to 5% by weight of the catalyst support, and still more particularly from 3.0% to 3.9% by weight of the catalyst support.

With respect to the barium promoter, the barium of the catalyst support is provided from a barium source. The barium source may be barium oxides, nitrates, carbonates, halogens, organic acids, and other barium salts which may be in their hydrated or non-hydrated forms. A specific example of a suitable barium source is BaCO$_3$. The barium source used in the synthesis or formation of the catalyst support may provide the final catalyst support with a barium oxide content in an amount of from 0.5% to 10% by weight of the catalyst support, more particularly from 1.0% to 3.0% by weight of the catalyst support, and still more particularly from 1.2% to 1.7% by weight of the catalyst support.

With respect to the zirconium promoter, the zirconium of the catalyst support is provided from a zirconium source. The zirconium source may be zirconium oxides, nitrates, carbonates, halogens, organic acids, and other zirconium salts, which may be in their hydrated or non-hydrated forms. A specific example of a suitable zirconium source is Zr(NO$_3$)$_3$.xH$_2$O. The zirconium source used in the synthesis or formation of the catalyst support may provide the final catalyst support with a zirconium oxide content in an amount of from 5% to 20% by weight of the catalyst support, more particularly from 9% to 16% by weight of the catalyst support, and still more particularly from 11.0% to 14.1% by weight of the catalyst support.

In preparing the catalyst support, the bayerite aluminum hydroxide support precursor material is mixed with the various promoter material sources described above and a sufficient amount of water to make a paste, dough or other plastic mass. This is then molded or shaped, such as through extrusion, into a desired shape to form a shaped body. The precursor material in powder form also can be tableted into for example ⅛" diameter tablets with a pressing pressure from 5,000 to 40,000 psig from 1 second to 2 minutes. The shaped body forming the support and resulting catalyst composition may be configured in various shapes and sizes. In one example, the shaped body for the support may be cylindrical in shape with a ⅛" diameter that may vary in length, such as ⅛" or less to up to several inches. In certain applications, the shape and size may be spherical or tablet-shaped or configured into other shapes, such as a star shape, with the thickness of the particle being of various thicknesses, which may be greater or less than ⅛" thick (e.g., 1/16" to ½").

The shaped body forming the catalyst support is then dried and calcined. Drying and calcination may be carried out in air, nitrogen, steam or other suitable gas. Drying may be carried out at room temperature or an elevated temperature (e.g., from 100° C. to 140° C.). The drying may also be included in the temperature ramp up used to reach the final calcination temperature. In many applications, the final calcination temperature will be a temperature of at least 750° C., with a final calcination temperature of from 800° C. to 1100° C. or from 900° C. to 1050° C. being particularly suitable.

In certain embodiments, a temperature ramp up during calcination with various soaking times at different intervals may be used to perform the calcination of the shaped body to form the final catalyst support. Temperature ramp up rates of from 1° C. to 10° C./min may be used with periodic soak times at various soak temperatures in the calcination gas may range from 0 to 5 hours or more. The catalyst support will typically be soaked at the final calcination temperature at from at least 1 hour or more and in many cases for several hours such as from 2 to 10 hours. An example of a suitable temperature ramp up and soak profile for the calcination of the catalyst support is provided in Table 1 below.

TABLE 1

| Ramp Temperature | Temperature Ramp Rate 1-10° C./min | Soak Time at Final Temp. 0-5 hour |
|---|---|---|
| 25-100° C. | 5° C./min | 1 hour |
| 100-150° C. | 5° C./min | 1-2 hours |
| 150-340° C. | 10° C./min | 0 hour |
| 340-350° C. | 1° C./min | 1-2 hours |
| 350-490° C. | 10° C./min | 0 hour |
| 490-800° C. | 10° C./min | 2-10 hours |

After calcination, the calcined catalyst support is allowed to cool to room temperature.

The formed catalyst support is then treated with a dehydrogenation catalyst component so that the final treated catalyst support contains the dehydrogenation catalyst component to form the final catalyst. The dehydrogenation catalyst component is meant to include those materials that are catalytically active, as well as those materials that may constitute promoters that promote the catalyst activity. This can include one or more different elements. Non-limiting examples of suitable dehydrogenation catalyst components that may be combined with the catalyst support include those described in U.S. Pat. No. 6,414,209 and U.S. patent application Ser. No. 13/742,439, filed Jan. 16, 2013, each of which is incorporated herein by reference in its entirety for all purposes.

In many embodiments, the dehydrogenation catalyst component includes platinum (Pt) and/or iridium (Ir) as an active catalyst component. Due to its availability, platinum may be used as the active catalyst component in many applications. The platinum may be combined with the catalyst support at a level of from 0.2% to 2% by weight of the catalyst. In particular embodiments, this component may be present in the catalyst composition at a level of from 0.5% to 1.5% by weight of the catalyst composition, and still more particularly from 0.7% to 1.2% by weight of the catalyst composition. Non-limiting examples of suitable sources of platinum that may be used in treating the catalyst support include chloroplatinic acid, platinous chloride and compounds containing the platinum ammine complex. By way of clarification, unless stated otherwise or is otherwise apparent from its context, all percentage amounts are based on weight percentages of the catalyst composition (the support together with the added metal or elements forming the dehydrogenation catalyst components without any optional binder materials).

Iron (Fe), cobalt (Co), nickel (Ni), and palladium (Pd) may also be as a dehydrogenation catalyst component. These materials may be combined with the catalyst support so that they are present in the catalyst composition so that their combined or total amount is at a level of from 0.2% to 15% by weight of the catalyst. In other words, if only one of these elements is used, that element may be present at a level anywhere within that range. If more than one of these elements is used the sum of their amounts will fall within this range. In particular embodiments, these components may be present in the catalyst composition at a level of from 1% to 3% by weight of the catalyst composition.

In certain embodiments the dehydrogenation catalyst component is platinum only. In others, the dehydrogenation catalyst component may be platinum and tin only. In still others the dehydrogenation catalyst component may be palladium only, or nickel only.

In certain embodiments, lithium (Li), sodium (Na), potassium (K), rubidium (Rb), cesium (Cs), francium (Fr) are combined with the catalyst support as a catalyst component. These materials may be combined with the catalyst support so that they are present in the catalyst composition where the combined or total amount is at a level of from 0.1% to 10% by weight of the catalyst, more particularly from 0.5% to 3% by weight of the catalyst.

Phosphorus (P), which acts as a promoter, may also be combined with the catalyst support in forming the catalyst composition. The phosphorus may be present in the catalyst composition at a level of from 1% to 9% by weight of the catalyst composition. In particular embodiments, the phosphorus is present at a level of from 1.1% to 1.7% by weight of the catalyst composition. Examples of suitable sources of phosphorus used in treating the support in preparing the catalyst may include, but are not limited to, phosphonic, phosphinous, phosphorus, and phosphoric acids, salts and esters of such acids, and phosphorous halides. In particular, phosphoric acid ($H_3PO_4$) and ammonium hydrogen phosphate (($NH_4$)$_2HPO_4$) may be used as the phosphorus source. Other examples include hypophosphorous acid, phosphorous acid, peroxomonophosphoric acid, hypophosphoric acid, pyrophosphoric acid, triphosphoric acid, and the like, as well as combinations comprising at least one of the foregoing.

Various other materials may be combined with the catalyst support to form the catalyst composition. Such materials may include at least one element from the group consisting of germanium (Ge), tin (Sn), lead (Pb), gallium (Ga), indium (In), and titanium (Ti). These materials may be present in the catalyst composition so that their combined or total amount is at a level of from 0.2% to 11% by weight of the catalyst. In particular embodiments, these components may be present in the catalyst composition where their total is at a level of from 1% to 4% by weight of the catalyst composition, and still more particularly from 2% to 3.5% by weight of the catalyst composition. Sources of these materials that may be used in treating the catalyst support include their nitrates, hydroxides, halides, carbonates, acetates, and other water soluble salts so that these materials are present in the final catalyst. In particular embodiments tin is used in the catalyst composition.

The catalyst may further include at least one element from the group consisting of magnesium (Mg), calcium (Ca), strontium (Sr), barium (Ba), lanthanum (La), as well as the other lanthanides. These materials may be present in the catalyst composition so that their combined or total amount is at a level of from 0.1% to 7% by weight of the catalyst composition. In particular embodiments, these components may be present so that their total amount is at a level of from 1% to 3% by weight of the catalyst composition, and still more particularly from 1.2% to 2.0% by weight of the catalyst composition. In particular embodiments, calcium and barium may be used in the catalyst. Various sources of these materials may be used in treating the catalyst support so that they are present in the final catalyst.

The catalyst composition may also include chlorine (Cl). The chlorine may be present in the catalyst composition at a level of from 0.1% to 2% by weight of the catalyst composition. In particular embodiments, the chlorine may be present at a level of from 0.15% to 1% by weight of the catalyst composition, and still more particularly from 0.17% to 0.6% by weight of the catalyst composition. The chlorine may be provided by other components or their sources that are combined with or used in treating the catalyst support, such as chloride salts of the various components. In other cases, it may be provided by a separate chlorine source, such as hydrochloric acid (HCl), which is used to treat the support.

In certain applications, manganese (Mn) can be incorporated into dehydrogenation catalyst, as described in U.S. patent application Ser. No. 13/742,439. The manganese may be present in any amount, however, in certain embodiments it is present in the catalyst composition at a level of from 0.05% to 5% by weight of the catalyst. In other applications, the manganese may be present in the catalyst composition at a level from 0.1% to 2.5% by weight of the catalyst. In particular embodiments, the manganese may be present at a level of from 0.1% to 1.0% by weight of the catalyst composition, and still more particularly from 0.2% to 0.3% by weight of the catalyst composition. Non-limiting examples of suitable sources of manganese include manganese oxides, as well as manganese nitrates, hydroxides, halides, carbonates, acetates, etc. Examples of manganese sources are also described in U.S. Pat. No. 4,547,618, which is incorporated herein by reference in its entirety for all purposes. Typically the manganese source is a manganese oxide or manganese carbonate, and is usually a salt that can be dissolved in water. These materials are applied to or otherwise combined with the catalyst support.

In developing the catalyst composition, the catalyst support is treated with the sources of the various materials described above. The various dehydrogenation catalyst components are typically dissolved in aqueous fluids that are then used to treat the catalyst support, such as through impregnation and incipient wetness, so that the catalyst support is impregnated with the solutions containing the dehydrogenation catalyst component(s).

In preparing the catalyst composition, a treatment solution may be made by adding the metal salts, phosphoric acid, chloride source (e.g., HCl), etc., and water together. The treatment solution may then be added all at once to the catalyst support, which is then mixed until the solution is adequately absorbed into the support. The wet alumina support may then be dried prior to calcining (e.g., 120° C. in air for one or more hours). The dried catalyst particle may then be calcined in air, nitrogen, steam, or other gas. The calcining may include ramping the temperature in various stages. For example, the impregnated catalyst support may be calcined at 500° C. in air for 5 hours with a ramp rate of 2-20° C./min.

In certain embodiments, the catalyst support as well as the final catalyst may contain no ruthenium.

The developed catalyst composition may be used in hydrocarbon conversion reactions, particularly in dehydrogenation reactions. In particular, the catalyst composition may be used in the dehydrogenation of those paraffins or alkane hydrocarbons of from $C_2$ to $C_{20}$, more particularly, those hydrocarbons of from $C_2$ to $C_5$, and still more particularly those from $C_3$ to $C_4$. The catalyst composition has particular application in the conversion of propane to propylene.

In use, the catalyst may be used in a reactor and contacted with a hydrocarbon feed that is introduced in the reactor under hydrocarbon conversion conditions to form hydrocarbon conversion products. The hydrocarbon feed may be a paraffin or alkane hydrocarbon feed and the conversion conditions may be those dehydrogenation reaction conditions useful to form dehydrogenated hydrocarbon products, such as a propane feed that is dehydrogenated to form propylene.

A steam co-feed is typically used in the reaction with the hydrocarbon feed. The steam may act as a carrier gas to facilitate introduction of the hydrocarbon into the reactor. The purpose of using steam is to carry heat into the reactor since the dehydrogenation is an endothermic reaction, so the thermal mass of steam helps to maintain the process temperature. Steam also helps to minimize coke formation. Steam is known to at least partially remove or inhibit coke formation on the catalyst. The steam also serves to dilute the hydrocarbon feed so the catalyst is not quickly coked and the reactor is not cooled too much due to the endothermic dehydrogenation reaction. Steam also serves as a diluent that shifts the equilibrium conversion to higher values. In certain applications, the hydrocarbon/$H_2O$ molar feed ratio may range from 1:1 to 1:10, more particularly from 1:2 to 1:6. A hydrocarbon/water molar feed of 1:3 to 1:5 has been found particularly useful for the dehydrogenation of propane.

The dehydrogenation reaction may be a non-oxidative dehydrogenation reaction wherein the reaction is carried out in an oxygen-free or substantially oxygen-free (i.e., no oxygen gas or $O_2$) environment. Furthermore, the reaction may be carried out without any hydrogen gas ($H_2$) co-feed, as is used in some dehydrogenation reactions. Diluents, which may be inert diluents, such as helium or nitrogen, may also be used in the reaction.

The feed streams may be preheated and introduced into the dehydrogenation reactor at temperatures that may range from 200° C. to 700° C. The hydrocarbon, steam and diluent feed may be introduced into the reactor at a GHSV of from 500 $h^{-1}$ to 4500 $h^{-1}$, more particularly from 3000 $h^{-1}$ to 3500 $h^{-1}$.

Because the dehydrogenation reaction is endothermic, heat input is typically required to maintain the reaction. The dehydrogenation reaction may be carried out in a tubular fixed bed reactor that is provided with a heat source to maintain suitable reaction temperatures. Other suitable reactors may be used however. The reaction temperatures are typically maintained at from 525° C. to 650° C., more particularly from 545° C. to 595° C.

After a period of use, the catalyst may be regenerated to remove coke buildup. In a typical regeneration cycle after dehydrogenation, an inert purge of the catalyst bed with $N_2$ is followed by the addition of dilute air (1-20 volume % $O_2$) to oxidize coke to either carbon monoxide or carbon dioxide or both for a specified period of time. Addition of steam during this period is optional. Once the regeneration or oxidation of coke is stopped an inert purge with $N_2$ is started again before starting the next dehydrogenation period. The time scales of $N_2$ purge and regeneration could vary anywhere from 10-180 minutes. In addition the temperatures during regeneration may be reduced to accommodate the temperature raise due to exothermic oxidation during the regeneration.

The catalyst composition of the invention does not tend to coke as readily as existing dehydrogenation catalyst compositions and has been found to provide high conversion and selectivity when used in dehydrogenation reactions. This produces a lower alkane recycle and a higher reaction throughput. The catalyst composition has been found to be particularly useful in providing a high conversion and selectivity in propane dehydrogenation. The lower-coking catalyst also allows the reactor to be run for longer periods of time during the dehydrogenation cycle between any necessary regenerations. This extends the life of the catalyst and reduces overall catalyst and product costs.

The following examples better serve to illustrate the invention.

EXAMPLES

Example 1

An alumina support was prepared by mixing 20.88 g of bayerite aluminum hydroxide with 0.702 g of La$(NO_3)_3 \cdot 6H_2O$, 1.39 g of Ce$(NO_3)_3 \cdot 6H_2O$, 0.32 g of $BaCO_3$, 3.76 g of Zr$(NO_3)_3 \cdot xH_2O$, and sufficient water to make a paste. The paste was extruded with a syringe to form an approximately ⅛" extrudate and calcined with the following ramping profile set forth in Table 2 below.

TABLE 2

| Ramp Temperature | Temperature Ramp Rate | Soak Time at Final Temp. |
|---|---|---|
| 25-100° C. | 5° C./min | 1 hour |
| 100-150° C. | 5° C./min | 1 hour |
| 150-340° C. | 10° C./min | 0 hour |
| 340-350° C. | 1° C./min | 1 hour |
| 350-490° C. | 10° C./min | 0 hour |
| 490-800° C. | 10° C./min | 5 hours |

After calcining, the alumina support was cooled. An eta (η) alumina phase was formed. The formed catalyst support was analyzed by XRF and had a composition of alumina (81.5 wt. %), $La_2O_3$ (1.6 wt. %), $CeO_2$ (3.3 wt. %), BaO (1.5 wt. %), and $ZrO_2$ (12.1 wt. %).

Example 2

The alumina support from Example 1 was treated with dehydrogenation catalyst components to form a final catalyst composition. A solution of the formulation set forth in Table 3 below was used to impregnate into 5 grams of the catalyst support prepared in Example 1.

TABLE 3

| Material | (grams) | (ml) |
|---|---|---|
| $H_3PO_4$ | 0.3 | — |
| HCl (Conc.) | — | 0.07 |
| Water | 2.34 | 2.34 |
| Ni$(NO_3)_2 \cdot 6H_2O$ | 0.07 | — |
| $SnCl_2 \cdot 2H_2O$ | 0.22 | — |
| Ca(NO3)2•4H2O | 0.56 | — |
| $H_2PtCl_6$ (aqueous at 20 wt. % Pt) | — | 0.18 |

After the catalyst solution was impregnated into the alumina catalyst support prepared in Example 1, the impregnated catalyst support was calcined at about 500° C. in air for about 5 hours with a ramp rate of 2-20° C./min. After the final soak period, the formed catalyst was cooled to room temperature and stored in dry nitrogen or dry air to keep the catalyst dry. This formed Catalyst A of Example 3 is discussed below.

Example 3

Catalyst A of Example 2 was used in a propane dehydrogenation reaction to form propylene. As a comparison, a commercial catalyst (Comparative Catalyst B) was also used in a propane dehydrogenation reaction at the same catalyst loading and at identical process conditions. Comparative Catalyst B was platinum (Pt) on an alumina support without any promoters, such as lanthanum (La), cerium (Ce), barium (Ba), or zirconium (Zr). Both catalysts produced about 92% selectivity. The conversion and time on stream are presented in FIG. 1. Each data point of FIG. 1 represents a cycle of use, wherein the catalysts were used in the dehydrogenation reaction and then regenerated before being used again.

As can be seen in FIG. 1, Catalyst A showed no decrease in conversion compared to Comparative Catalyst B. The performance improvement for Catalyst A can be seen in the lower coking properties of the catalyst versus Comparative Catalyst B. The conversion dropped as coke built up on the catalyst surface and covered the platinum particles, preventing the dehydrogenation reaction from occurring. A more rapid decrease in conversion indicates a more rapid buildup of coke on the catalyst surface.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of forming a dehydrogenating catalyst comprising:
   forming a mixture comprising a bayerite aluminum hydroxide (Al(OH)$_3$), a lanthanum (La) source, a cerium (Ce) source, a barium (Ba) source, a zirconium (Zr) source, and water into a shaped body;
   calcining the shaped body at a temperature of at least 750° C. to form a catalyst support;
   treating the catalyst support with a dehydrogenation catalyst component to form a treated catalyst support containing the dehydrogenation catalyst component; and
   calcining the treated catalyst support.

2. The method of claim 1, wherein;
   the dehydrogenation catalyst component is comprised of at least one of platinum (Pt), tin (Sn), nickel (Ni), phosphorus (P), and calcium (Ca).

3. The method of claim 1, wherein:
   the catalyst support contains lanthanum oxide in an amount of from 1% to 8% by weight of the catalyst support provided by the lanthanum source of the mixture.

4. The method of claim 1, wherein:
   the catalyst support contains cerium oxide in an amount of from 1% to 8% by weight of the catalyst support provided by the cerium source of the mixture.

5. The method of claim 1, wherein:
   the catalyst support contains barium oxide in an amount of from 0.5% to 10% by weight of the catalyst support provided by the barium source of the mixture.

6. The method of claim 1, wherein:
   the catalyst support contains zirconium oxide in an amount of from 5% to 20% by weight of the catalyst support provided by the zirconium source of the mixture.

7. The method of claim 1, wherein:
   the catalyst support contains lanthanum oxide in an amount of from 1% to 8% by weight of the catalyst support provided by the lanthanum source of the mixture, cerium oxide in an amount of from 1% to 8% by weight of the catalyst support provided by the cerium source of the mixture, barium oxide in an amount of from 0.5% to 10% by weight of the catalyst support provided by the barium source of the mixture, and zirconium oxide in an amount of from 5% to 20% by weight of the catalyst support provided by the zirconium source of the mixture.

8. The method of claim 1, wherein:
the catalyst support is in a substantially eta alumina phase.

9. A method of dehydrogenating paraffin hydrocarbons comprising:
contacting a paraffin hydrocarbon feed with a catalyst within a reactor in the presence of steam under dehydrogenation reaction conditions suitable to form dehydrogenated hydrocarbon products, the catalyst being that formed by a method comprising:
forming a mixture comprising a bayerite aluminum hydroxide ($Al(OH)_3$), a lanthanum (La) source, a cerium (Ce) source, a barium (Ba) source, a zirconium (Zr) source, and water into a shaped body;
calcining the shaped body at a temperature of at least 750° C. to form a catalyst support;
treating the catalyst support with a dehydrogenation catalyst component to form a treated catalyst support containing the dehydrogenation catalyst component; and
calcining the treated catalyst support.

10. The method of claim 9, wherein;
the dehydrogenation catalyst component is comprised of at least one of platinum (Pt), tin (Sn), nickel (Ni), phosphorus (P), and calcium (Ca).

11. The method of claim 9, wherein:
the catalyst support contains lanthanum oxide in an amount of from 1% to 8% by weight of the catalyst support provided by the lanthanum source of the mixture.

12. The method of claim 9, wherein:
the catalyst support contains cerium oxide in an amount of from 1% to 8% by weight of the catalyst support provided by the cerium source of the mixture.

13. The method of claim 9, wherein:
the catalyst support contains barium oxide in an amount of from 0.5% to 10% by weight of the catalyst support provided by the barium source of the mixture.

14. The method of claim 9, wherein:
the catalyst support contains zirconium oxide in an amount of from 5% to 20% by weight of the catalyst support provided by the zirconium source of the mixture.

15. The method of claim 9, wherein:
the catalyst support contains lanthanum oxide in an amount of from 1% to 8% by weight of the catalyst support provided by the lanthanum source of the mixture, cerium oxide in an amount of from 1% to 8% by weight of the catalyst support provided by the cerium source of the mixture, barium oxide in an amount of from 0.5% to 10% by weight of the catalyst support provided by the barium source of the mixture, and zirconium oxide in an amount of from 5% to 20% by weight of the catalyst support provided by the zirconium source of the mixture.

16. The method of claim 9, wherein:
the catalyst support is in a substantially eta alumina phase.

17. A dehydrogenation catalyst composition useful for the dehydrogenation of hydrocarbons, the catalyst composition comprising:
a catalyst support of bayerite aluminum hydroxide ($Al(OH)_3$) having a substantially eta alumina phase and containing lanthanum (La), cerium (Ce), barium (Ba), and zirconium (Zr) synthesized within the crystal structure of the catalyst support.

* * * * *